United States Patent [19]

Lin

[11] Patent Number: 4,701,513
[45] Date of Patent: Oct. 20, 1987

[54] NOVEL EPOXY HARDENERS

[75] Inventor: Shiow C. Lin, Ellicott City, Md.

[73] Assignee: W. R. Grace & Co., New York, N.Y.

[21] Appl. No.: 941,864

[22] Filed: Dec. 15, 1986

[51] Int. Cl.$^4$ .............................................. C08G 59/44
[52] U.S. Cl. ................... 528/89; 525/329.3;
525/332.9; 525/375; 528/91; 528/92; 528/93;
528/94; 528/117; 528/312; 528/313; 528/314;
528/315; 528/319; 528/323; 528/109
[58] Field of Search ............... 528/117, 323, 89, 91,
528/92, 93, 94, 312, 313, 314, 315, 319, 109;
525/332.9, 329.3, 375

[56] References Cited

U.S. PATENT DOCUMENTS

| | | | |
|---|---|---|---|
| Re. 29,027 | 11/1976 | Alford et al. | 528/117 X |
| 3,622,540 | 11/1971 | Hashimoto et al. | 528/117 X |
| 3,640,957 | 2/1972 | Tomalia et al. | 528/117 |
| 3,749,683 | 7/1973 | Tomalia et al. | 528/117 |
| 4,119,679 | 10/1978 | Nishizawa et al. | 528/117 X |
| 4,600,763 | 7/1986 | Goel | 528/117 X |

OTHER PUBLICATIONS

"Polymerization with Expansion in Volume" in ACS Symposium Series, Ring Opening Polymerization, pp. 38–41, vol. 59 (1977).
"Polymeric Materials Science and Engineering", M. S. Cohen et al., vol. 54, pp. 12–17 (1986).
Angew. Chem. Internat. Edit., R. Nehring and W. Seeliger, vol. 9, pp. 460, 461 (1970).

Primary Examiner—Earl Nielsen
Attorney, Agent, or Firm—Richard P. Plunkett; William W. McDowell, Jr.

[57] ABSTRACT

This invention relates to the use of compositions of the formula:

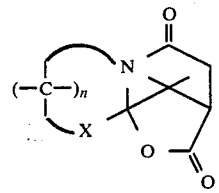

wherein n is 2 to 4 and X is —O—, —S— or

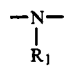

wherein $R_1$ is an aliphatic or aromatic moiety as a curing agent for epoxy resins to form a thermoset material which has a reduced shrinkage.

5 Claims, 1 Drawing Figure

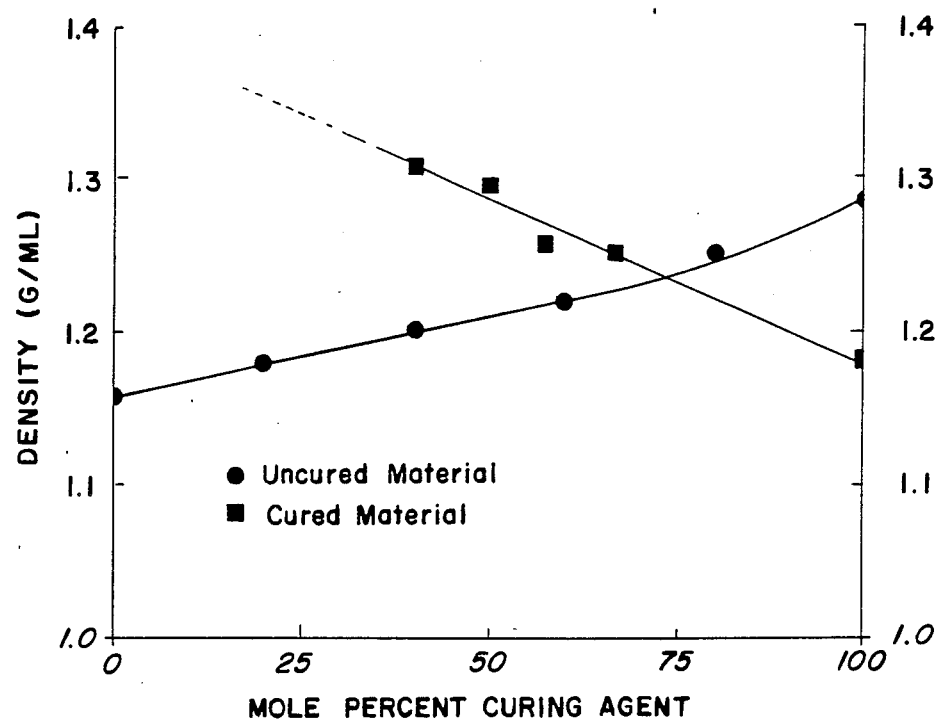

NOVEL EPOXY HARDENERS

BACKGROUND OF THE INVENTION

1. Field of the Invention

This invention relates to novel epoxy resin curing agents which afford reduced shrinkage to the epoxy resin on curing to a thermoset material.

2. Description of the Prior Art

A general concern of polymerization is the volume reduction resulting in the development of internal stresses in a polymeric material. For a thermoplastic this concern of polymerization shrinkage may not be as serious as in thermosets due to the fact that a final fabrication step is required to turn a polymer into a useful material, which usually relieves the build-up of internal stresses. However, a thermoset cannot be further fabricated to release the internal stress through a remelt process. As a result of the entrapped internal stresses in a thermoset, the molded part may experience premature failure when exposed to normal environmental conditions. This phenomenon has been shown in several application areas such as the reduction of adhesion, the failure of interfacial bonding of a matrix and fibers in a composite, and the cracking of a casting compound. Therefore, a thermoset with a zero shrinkage is desirable in many important industrial applications.

Ring opening polymerization usually involves less shrinkage than simple addition polymerization. If the ring is large enough, no shrinkage should be involved in the polymerization. Based on this concept. a bicyclic compound, a ketal-lactone Structure (1), was prepared and polymerized with either boron trifluoride or a base to a polyester without change in volume [Bailey et al-"Polymerization with Expansion Volume" in ACS Symposium Series, "Ring Opening Polymerization", p. 38, vol. 59 (1977)]:

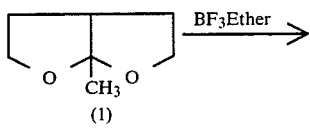
(1)

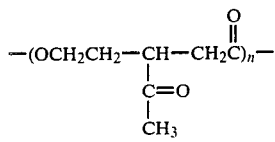

The spiroorthocarbonate first invented by Bailey has been seriously considered for development into a commercial product for coatings, adhesives and related polymeric materials. The materials were based on a blend of epoxy resins and the spiroorthocarbonate. It was concluded that the corrosion resistance of steel was significantly improved by the coating containing polymerized spiroorthocarbonate due to the reduced shrinkage, and hence, internal stress (M. S. Cohen et al, Polymeric Materials Science and Engineering, vol. 54, 12 (1986).

A compund having a Structure (2) was prepared simply by reacting a 2-isopropyl-2-oxazoline and maleic anhydride in ethylenedichloride at reflux conditions [R. Nehring and W. Seeliger, Angew. Chem. internat. Edit., vol. 9, 460 (1970)]:

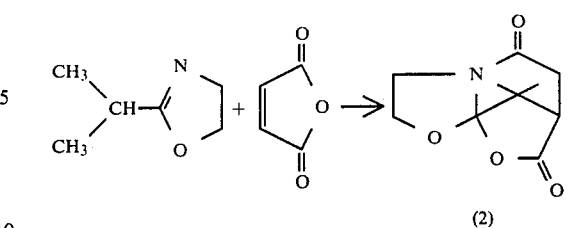
(2)

The product was described to undergo thermal polymerization when heated at 180° to 200° C. for 20 minutes in the absence of moisture. The reaction produces a poly(ester-imide), a transparent plastic of high molecular weight which is soluble in a number of solvents such as DMF, dioxane, DMSO, ethylenedichloride and pyridine [R. Nehring and W. Seeliger, Angew. Chem. Intern. Edit., vol. 9, 461 (1970)].

OBJECTS OF THE INVENTION

One object of the invention is to produce a thermoset material from an epoxy resin and a new class of hardeners therefor. Another object of the invention is to develop a new class of epoxy hardeners from maleic anhydride and 2-oxazoline. A further object of the instant invention is to develop a new class of epoxy hardeners which also undergo homopolymerization. Yet another object of the instant invention is to develop a new class of epoxy hardeners which have low shrinkage potential during the crosslinking process. These and further objects will become apparent from a reading hereinafter.

SUMMARY OF THE INVENTION

This invention relates to the use of compositions of the formula:

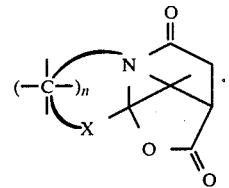

wherein n is 2 to 4 and X is —O—, —S— or

wherein $R_1$ is an aliphatic or aromatic moiety as a curing agent for epoxy resins to form a thermoset material which has a reduced shrinkage.

The novel epoxy hardeners of the instant invention are added to an epoxy resin in amounts ranging from 0.1 up to 99.9% by weight of the epoxy resin. The materials are then heated to a temperature of at least 150° C. (preferably to 175° C.) for periods ranging from 1 to 5 days or more in order to obtain a thermoset product with reduced shrinkage.

The curing period can be shortened and the curing temperature reduced by the addition of known anionic and cationic catalysts or curing rate accelerators such as organometallics, Lewis bases and Lewis acids. Examples of organometallics operable herein include, but are not limited to, stannous octoate, dibutyltin oxide and dibutyltin dilaurate. Operable Lewis bases include, but are not limited to, N,N-dimethylaniline, triphenylphosphine and triethylamine. Operable Lewis acids include, but are not limited to, $BF_3$ complexes such as $BF_3$.monoethylamine. With the addition of these catalyst systems the curing temperature can be lowered to about 120° C. and a full cure is obtained in about 30 minutes.

The epoxy resin used herein to form a cured thermoset material comprises those materials possessing more than one epoxy group, i.e.,

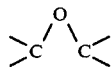

group. These compounds may be saturated or unsaturated, aliphatic, cycloaliphatic, aromatic or heterocyclic and may be substituted with substituents, such as chlorine hydroxyl groups, ether radicals and the like. They may be monomeric or polymeric.

For clarity, many of the polyepoxides and particularly those of the polymeric type are described in terms of epoxy equivalent values. That is, many of the polyepoxides will be referred to hereinafter in terms of their epoxy equivalency. The term "epoxy equivalency" refers to the number of epoxy groups contained in the average molecule of the desired material. The epoxy equivalency is obtained by dividing the average molecular weight of the polyepoxide by the epoxide equivalent weight. The epoxide equivalent weight is determined by heating 1 gram sample of the polyepoxide with an excess of pyridinium chloride dissolved in pyridine at the boiling point for 20 minutes. The excess pyridinium chloride is then back titrated with 0.1N sodium hydroxide to phenolphtalein end point. The epoxide value is calculated by considering one HCl as an equivalent of one epoxide. This method is used to obtain all epoxide values reported herein.

If the polyepoxides are single monomeric compounds having all of their epoxide groups intact, their epoxy equivalency will be whole integers, such as 1, 2, 3, 4 and 5. However, in the case of the polymeric type polyepoxides many of the materials may contain some of the monomeric monoepoxides or have some of their epoxy groups hydrated or otherwise reacted and/or contain macromolecules of somewhat different molecular weight so the epoxy equivalent values may be quite low and contain fractional values. The polymeric material may, for example, have epoxy equivalent values, such as 1.5, 1.8, 2.5 and the like. The polyepoxides used in the present composition and process are those having an epoxy equivalency of at least 1.0.

Various examples of polyepoxides that may be used in the composition and process of this invention are given in U.S. Pat. No. 2,633,458, and it is to be understood that so much of the disclosure of that patent relative to examples of polyepoxides is incorporated by reference into this specification.

Other examples include the epoxidized esters of the polyethylenically unsaturated monocarboxylic acids, such as epoxidized linseed, soybeen, perilla, oiticica, tung, walnut and dehydrated castor oil, methyl linoleate, butyl linoleate, ethyl 9,12-octadecadienoate, butyl 9,12,15-octadecatrienoate, butyl eleostearate, monoglycerides of tung oil fatty acids, monoglycerides of soybean oil, sunflower, rapeseed, hempseed, sardine, cottonseed oil and the like.

Another group of the epoxy-containing materials used in the composition and process of this invention include the epoxidized ester of unsaturated monohydric alcohols and polycarboxylic acids. For example, di(2,3-epoxybutyl)adipate, di(2,3-epoxybutyl)oxalate, di(2,3-epoxyhexyl)succinate, di(3,4-epoxybutyl)maleate, di(2,3-epoxyoctyl)pimelate, di(2,3-epoxybutyl)phthalate, di(2,3-epoxyoctyl)tetrahydrophthalate, di(4,5-epoxydodecyl)maleate, di(2,3-epoxybutyl)tetraphthalate, di(2,3-epoxypentyl) thiodipropionate, di(5,6-epoxytetradecyl)diphenyldicarboxylate, di(3,4-epoxyheptyl)sulfonyldibutyrate, tri(2,3-epoxybutyl)1,2,4-butanetricarboxylate, di(5,6-epoxypentadecyl)tartarate, di(4,5-epoxytetradecyl)maleate, di(2,3-epoxybutyl)azelate, di(3,4-epoxybutyl)citrate, di(5,6-epoxyoctyl)cyclohexane-1,2-dicarboxylate, di(4,5-epoxyoctadecyl)malonate.

Still another group comprises the epoxidized polyethylenically unsaturated hydrocarbons, such as epoxidized 2,2-bis(2-cyclohexenyl)propane, epoxidized vinyl cyclohexene and epoxidized dimer of cyclopentadiene.

Another group comprises the epoxidized polymers and copolymers of diolefins, such as butadiene. Examples of this include, among others, butadiene-acrylonitrile copolymers (Hycar rubbers), butadiene-styrene copolymers and the like.

Another group comprises the glycidyl containing nitrogen compounds, such as diglycidyl aniline and di- and triglycidylamine.

The polyepoxides that are particularly preferred for use in the compositions of the invention are the glycidyl ethers and particularly the glycidyl ethers of polyhydric phenols and polyhydric alcohols. The glycidyl ethers of polyhydric phenols are obtained by reacting epichlorohydrin with the desired polyhydric phenols in the presence of alkali. Polyether-A and Polyether-B described in the above noted U.S. Pat. No. 2,633,458 are good examples of polyepoxides of this type. Other examples include the polyglycidyl ether of 1,1,2,2-tretrakis(4-hydroxyphenyl)ethane (epoxy value of 0.45 eq./100 g) and melting point 85° C., polyglycidyl ether of 1,1,5,5-tetrakis(hydroxyphenyl)pentane (epoxy value of 0.514 eq. (100 g) and the like and mixtures thereof.

Additional examples of epoxy resins operable herein include, but are not limited to, diglycidyl isophthalate, diglycidyl phthalate, o-glycidyl phenyl glycidyl ether, diglycidyl ether of resorcinol, triglycidyl ether of phloroglucinol, triglycidyl ether of methyl phloroglucinol, 2,6-(2,3-epoxypropyl)phenylglycidyl ether, 4-(2,3-epoxy)propoxy-N,N-bis(2,3-epoxypropyl)aniline, 2,2-bis[p-2,3-epoxypropoxy)phenyl]-propane, diglycidyl ether of bisphenol-A, diglycidyl ether of bisphenolhexafluoroacetone, diglycidyl ether of 2,2-bis(4-hydroxyphenyl)nonadecane, diglycidyl phenyl ether, triglycidyl 4,4-bis(4-hydroxyphenyl)pentanoic acid, diglycidyl ether of tetrachlorobisphenol-A, diglycidyl ether of tetrabromobisphenol-A, triglycidyl ether of trihydroxybiphenyl, tetraglycidoxy biphenyl, [tetrakis(2,3-epoxypropoxy)diphenylmethane], 2,2,4,4'-tetrakis(2,3-epoxypropoxy)benzophenone, 3,9-bis[2-(2,3-epoxypropoxy)-phenylethyl]-2,4,8,10-tetraoxaspiro[5,5]undecane, triglycidoxy-1,1,3-triphenylpropane, tetraglycidoxy tetraphenylethane, polyglycidyl ether of phenolformaldehyde novolac, polyglycidyl ether of o-cresol-formaldehyde novolac, diglycidyl ether of butanediol, di(2-methyl)glycidyl ether of ethylene glycol, polyepichlorohydrin di(2,3-epoxypropyl)ether, diglycidyl ether of polypropylene glycol, epoxidized polybutadiene, epoxidized soybean oil, triglycidyl ether of glycerol, triglycidyl ether of trimethylol-propane, polyallyl glycidyl ether, 2,4,6,8,10-pentakis-[3-(2,3-epoxypropoxy)propyl]2,4,6,8,10-pentamethylcyclopentasiloxane, diglycidyl ether of chlorendic diol, diglycidyl ether of dioxanediol, diglycidyl ether of endomethylene cyclohexanediol, diglycidyl ether of hydrogenated bisphenol-A, vinylcyclohexene dioxide, limonene dioxide, dicyclopentadiene dioxide, p-epoxycyclopentenylphenyl glycidyl ether, epoxydicyclopentenylphenyl glycidyl ether, o-epoxycyclopentenylphenylglycidyl ether, bis-epoxydicyclopentyl ether of ethylene glycol, [2-3,4-epoxy)cyclohexyl-5,5-spiro(3,4-epoxy)cyclohexane-m-dioxane], 1,3-bis[2,3-epoxypropoxy)propyl]tetramethyldisiloxane, epoxidized polybutadiene, triglycidyl ester of linoleic trimer acid, epoxidized soybean oil, diglycidyl ester of linoleic dimer acid, 2,2-bis[4-(2,3-epoxypropyl)-cyclohexyl]propane, 2,2-(4-[3-chloro-2-(2,3-epoxypropoxy)propolyl]-cyclohexyl)propane, 2,2-bis(3,4-epoxycyclohexyl)propane, bis(2,3-epoxycyclopentyl)ether (liquid isomer), bis(2,3-epoxycyclopentyl)ether (solid isomer), 1,2-epoxy-6-(2,3-epoxypropoxy)hexahydro-4,7-methanoindane, 3,4-epoxycyclohexylmethyl-(3,4-epoxy)cyclohexane carboxylate, 3,4-epoxy-6-methylcyclohexylmethyl-4-epoxy-6-methylcyclohexane carboxylate and bis(3,4-epoxy-6-methylcyclohexylmethyl)adipate. Tri- and tetrafunctional epoxides such as triglycidyl isocyanurate and tetraphenylolethane epoxy are also operable herein.

The following examples will aid in explaining, but expressly not limit, the instant invention. Unless otherwise noted, all parts and percentages are by weight.

EXAMPLE 1

Preparation of Tricyclic Dimethyloxazoline—Lactam-Lactone 1 mole of maleic anhydride was dissolved in 500 ml of ethylene dichloride solvent in a round bottom flask equipped with stirrer and heating mantle. One mole of 2-isopropyl-4,4-dimethyl 2-oxazoline was slowly added over a 30-minute period at 30° C. As soon as the oxazoline addition started, the solution immediately became clear, gradually turning to yellow, then gold. Upon complete addition of the oxazoline, the solution was heated at reflux for 40 minutes. The heat was removed from the flask and the flask attached to a rotary evaporator to remove any solvent present. The flask was then placed in an ice bath wherein crystals of 4,4,11,11-tetramethyl-2,10-dioxa-5-azatricyclo[6.2.1.0]undecane-6,9-dione; that is:

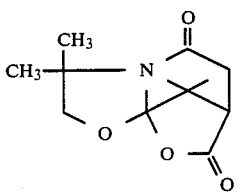
(A)

were formed. This product will hereinafter be referred to as curing agent (A).

A similar reaction was carried out except that 1 mole of 2-isopropyl 2-oxazoline was substituted for the 2-isopropyl-4,4-dimethyl 2-oxazoline in Example 1. The resultant crystallized product, i.e., 11,11-dimethyl-2,10-dioxa-5-azatricyclo[6.2.1.0]undecane-6,9-dione, had the formula:

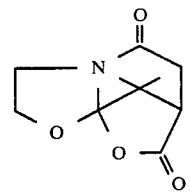

This product will hereinafter be referred to as curing agent (B).

EXAMPLE 2

In order to demonstrate the curability of the instant curing agents, mixtures of various epoxy resins and varying amounts of the aforesaid curing agents (A) and (B) were blended and then cured at 175° C. The curing conditions and results are shown in TABLE I:

TABLE I

| Mixture | Curing Agent | Epoxy Resin | Curing Agent/Epoxy | Cure at 175° C. |
|---|---|---|---|---|
| 1 | A | Epon-828[1] | 1 mole: 1 mole | 4 days |
| 2 | A | Epon-828 | 2 mole: 1 mole | 4 days |
| 3 | B | Epon-828 | 1 mole: 1 mole | 4 days |
| 4 | B | Epon-828 | 2 mole: 1 mole | 4 days |
| 5 | A | Araldite CY-179[2] | 1 mole: 1 mole | 3 days |
| 6 | A | Araldite EPN-1139[3] | 1 mole: 1 mole | 3 days |
| 7 | A | Araldite MY-720[4] | 1 mole: 1 mole | 30 minutes |
| 8 | A | Lekutherm KU-6552[5] | 1 mole: 1 mole | 1 day |

[1]Diglycidyl ether of Bisphenol-A commercially available from Shell Chemical Corp.
[2]A cycloaliphatic epoxy resin commercially available from Ciba-Geigy Corp.
[3]An epoxy novolac resin commercially available from Ciba-Geigy Corp.
[4]A multifunctional epoxy resin commercially available from Ciba-Geigy Corp.
[5]A cycloaliphatic epoxy resin commercially available from Mobay Chemical Corp.

EXAMPLE 3

2.4 g of curing agent (A) from Example 1 was admixed with 3.8 g of diglycidyl ether of bisphenol-A commercially available from Shell Chemical Corp. under the tradename "Epon-828". The mixture was well mixed and placed in an oven heated to 175° C. After 4 days the material cured resulting in a clear, dark brown, crosslinked plastic that was tough and flexible.

EXAMPLE 4

The materials and procedures in Example 3 were repeated but 3.8 g of Epon-828 were combined with 4.8 g of curing agent (A). After a 4-day cure, the resulting, crosslinked material was a tough, dark brown material which could not be remelted.

EXAMPLE 5

The procedure of Example 3 was repeated except that 2.1 g of curing agent (B) from Example 1 was admixed with 3.8 g of Epon-828. Following a 4-day cure at 175° C. the resulting, crosslinked material was a tough, brown thermoset that was infusible.

EXAMPLE 6

Example 5 was repeated except that 3.8 g of Epon-828 were admixed with 4.2 g of curing agent (B). After a 4-day cure at 175° C., the resultant material was a tough, dark brown thermoset which could not be remelted.

EXAMPLE 7

The procedure of Example 3 was repeated except that 1.19 g of curing agent (A) was admixed with 1.37 g of a commercially available, cycloaliphatic epoxy resin manufactured by Ciba-Geigy Corp. under the tradename "Araldite CY-179". After 3 days at 175° C., a brown thermoset product resulted which was infusible.

EXAMPLE 8

Using the procedure of Example 3, 0.96 g of curing agent (A) was admixed with 2.06 g of an epoxy novolac resin commercially available from Ciba-Geigy Corp. under the tradename "Araldite EPN-1139". After 3 days at 175° C., the resultant thermoset material was dark brown in color and was infusible.

EXAMPLE 9

Using the procedure of Example 3, 0.96 g of curing agent (A) was admixed with 2.0 g of a multifunctional epoxy resin commercially available from Ciba-Geigy Corp. under the tradename "Araldite MY-720". After curing for 30 minutes at 175° C., a dark brown thermoset resulted which was infusible.

EXAMPLE 10

The procedure of Example 3 was repeated using 0.72 g of curing agent (A) and 3.15 g of a cycloaliphatic epoxy resin commercially available from Mobay Chemical Corp. under the tradename "Lekutherm KU-6552". After 24 hours at 175° C. a thermoset resulted which was extremely flexible and tough and ould not be remelted.

One of the main advantages of using the instant epoxy curing agents is their availability to expand on polymerization during the curing reaction and thereby offsetting the shrinkage afforded by the epoxy resin resulting in a thermoset product having a reduced shrinkage.

EXAMPLE 11

In order to demonstrate the actual volume expansion properties of mixtures containing the instant curing agents and epoxy resin, several samples containing varying amounts of curing agent were cured for 96 hours. Following this cure, the densities of the materials were checked through the use of a pycnometer, using helium as the carrier gas. The epoxy resin used in each case was Epon-828, and the curing agent was curing agent (A). The results are set out in TABLE II:

TABLE II

| Mixture | Mol. Ratio Curing Agent/Epoxy | Cured Density g/mol |
|---|---|---|
| 1 | 2/3 | 1.306 |
| 2 | 1/1 | 1.292 |
| 3 | 4/3 | 1.260 |
| 4 | 2/1 | 1.254 |
| 5 | 1/0 | 1.182 |

When the densities of the cured mixtures are compared to the calculated densities of the uncured products, the effects of the ring opening polymerization of the instant curing agents can be observed. These data are presented in the FIGURE. The FIGURE shows that the density of the cured resins decreases as the amount of curing agents increases, and the density of the uncured product behaves in the opposite fashion. That is, at high curing agent loadings, the final densities are lower than those of the initial material indicating that volume expansion has occurred.

EXAMPLE 12

The following examples set out in TABLE III show a reduced curing period when known anionic and cationic initiators are added to an epoxy resin and hardener of the instant invention. In all the examples in TABLE III the epoxy resin (Epon-828) was admixed with an equal weight of curing agent (A). The known curing agents herein referred to as cured accelerators were added in an amount equal to about 0.5% of the weight of the epoxy resin. The results are shown in TABLE III:

TABLE III

| Resin | Cure Accelerator | Cure Time |
|---|---|---|
| Epon-828 | — | 96 hours |
| Epon-828 | Tip Octoate | 0.75 hour |
| Epon-828 | DABCO | 0.75 hour |
| Epon-828 | t-Butyl Tin Dilaurate | 6 hours |
| Epon-828 | Triphenylphosphine | 2 hours |
| Epon-828 | Pyridine | 0.75 hour |
| Epon-828 | Dimethylbenzylamine | 0.75 hour |
| Epon-828 | BF$_3$ monoethylamine | 0.5 hour |
| Epon-828 | Dipehnyliodonium tetrafluoroborate | 24 hours |
| Epon-828 | Diphenyliodonium hexafluorophosphate | 27 hours |

I claim:

1. A thermosettable composition comprising an epoxy resin and 0.1 to 99.9% by weight of the epoxy resin of an epoxy hardener of the formula:

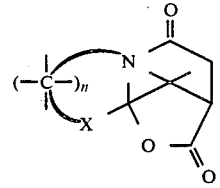

wherein n is 2 to 4 and X is —O—, —S— or

wherein $R_1$ is an aliphatic or aromatic moiety.

2. The composition of claim 1 wherein the epoxy hardener is:

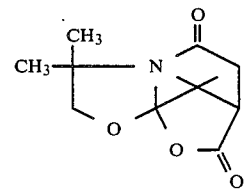

3. The composition of claim 1 wherein the epoxy hardener is:

9

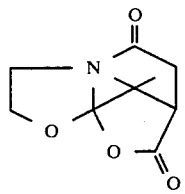

4. The composition of claim 1 containing in addition an anionic or cationic curing rate accelerator.

5. The composition of claim 4 wherein the curing rate accelerator is selected from the group consisting of tin octoate, t-butyl tin dilaurate, triphenylphosphine, pyridine, dimethylbenzylamine, BF$_3$ monoethylamine, diphenyliodonium tetrafluoroborate and diphenyliodonium hexafluorophosphate.

* * * * *

10

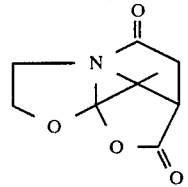

4. The composition of claim 1 containing in addition an anionic or cationic curing rate accelerator.

5. The composition of claim 4 wherein the curing rate accelerator is selected from the group consisting of tin octoate, t-butyl tin dilaurate, triphenylphosphine, pyridine, dimethylbenzylamine, BF$_3$ monoethylamine, diphenyliodonium tetrafluoroborate and diphenyliodonium hexafluorophosphate.

* * * * *

UNITED STATES PATENT AND TRADEMARK OFFICE
CERTIFICATE OF CORRECTION

PATENT NO. : 4,701,513

DATED : October 20, 1987

INVENTOR(S) : Shiow Ching Lin

It is certified that error appears in the above-identified patent and that said Letters Patent is hereby corrected as shown below:

<u>In the Claims</u>:

In column 10, lines 1-15, delete Claims 4 and 5, which are a duplicate of the identical Claims 4 and 5 in column 9.

Signed and Sealed this

Twenty-third Day of February, 1988

Attest:

DONALD J. QUIGG

Attesting Officer     Commissioner of Patents and Trademarks